(12) United States Patent
Ferris

(10) Patent No.: US 9,186,283 B2
(45) Date of Patent: Nov. 17, 2015

(54) WOUND DRESSING

(71) Applicant: Matthew G. Ferris, Mendon, NY (US)

(72) Inventor: Matthew G. Ferris, Mendon, NY (US)

(*) Notice: Subject to any disclaimer, the term of this patent is extended or adjusted under 35 U.S.C. 154(b) by 177 days.

(21) Appl. No.: 13/861,687

(22) Filed: Apr. 12, 2013

(65) Prior Publication Data
US 2013/0281951 A1 Oct. 24, 2013

Related U.S. Application Data

(60) Provisional application No. 61/635,320, filed on Apr. 19, 2012.

(51) Int. Cl.
| A61F 13/00 | (2006.01) |
| A61F 13/538 | (2006.01) |
| A61F 13/60 | (2006.01) |
| A61F 13/02 | (2006.01) |

(52) U.S. Cl.
CPC ............ *A61F 13/538* (2013.01); *A61F 13/022* (2013.01); *A61F 13/0213* (2013.01); *A61F 13/60* (2013.01)

(58) Field of Classification Search
CPC ........................... A61F 13/0213; A61F 13/022
USPC .......................................................... 604/368
See application file for complete search history.

(56) References Cited

U.S. PATENT DOCUMENTS

| 2,629,378 A | * | 2/1953 | Barton ........................... 604/307 |
| 4,499,896 A | * | 2/1985 | Heinecke ........................ 602/47 |
| 4,600,001 A | * | 7/1986 | Gilman ........................... 602/52 |
| 4,664,106 A | * | 5/1987 | Snedeker ........................ 602/57 |
| 5,152,282 A | | 10/1992 | Elphick |
| 5,160,315 A | * | 11/1992 | Heinecke et al. ............... 602/57 |
| 5,380,294 A | * | 1/1995 | Persson ......................... 604/180 |
| 5,495,856 A | * | 3/1996 | Fentress ........................ 128/846 |
| 5,713,842 A | * | 2/1998 | Kay ................................ 602/57 |
| 5,792,089 A | | 8/1998 | Penrose |
| 6,242,665 B1 | | 6/2001 | Malowaniec |
| 6,685,682 B1 | * | 2/2004 | Heinecke et al. ............. 604/307 |
| 6,832,611 B2 | | 12/2004 | Altman |
| 6,834,652 B2 | | 12/2004 | Altman |
| 6,875,199 B2 | | 4/2005 | Altman |
| 6,893,422 B2 | | 5/2005 | Altman |
| 6,977,323 B1 | | 12/2005 | Swenson |

(Continued)

FOREIGN PATENT DOCUMENTS

| EP | 2572737 A1 * | 3/2013 |
| WO | WO 2011008360 A1 * | 1/2011 |
| WO | WO 2011121394 A1 * | 10/2011 |

*Primary Examiner* — Susan Su
(74) *Attorney, Agent, or Firm* — Harris Beach PLLC; Neal L. Slifkin

(57) ABSTRACT

A wound dressing is provided which includes an inner layer with a plurality of drain holes around the perimeter. The inner layer is resistant to penetration by liquid. Adjacent the inner layer is an absorbent layer. An outer layer is adjacent, but not attached to the absorbent layer. The outer layer is resistant to penetration by liquid. The outer layer includes an adhesive band. A removable protective layer covers the adhesive bands and includes a plurality of perforations spaced about the protective layer with a plurality of non-perforated sections between the perforations such that when removed, the perforations cause separation at the perforations and only one non-perforated section is removed at a time. A base layer is provided with an open area and adhesive bands. The base layer is attached to the skin and the outer layer covers the open area of the base layer.

12 Claims, 4 Drawing Sheets

(56) References Cited

U.S. PATENT DOCUMENTS

| | | |
|---|---|---|
| 7,074,981 B2 | 7/2006 | Chalmers |
| 7,135,606 B1 * | 11/2006 | Dozier et al. .................. 602/57 |
| 7,612,248 B2 * | 11/2009 | Burton et al. .................. 602/58 |
| 7,723,561 B2 * | 5/2010 | Propp .............................. 602/58 |
| 2002/0169405 A1 * | 11/2002 | Roberts ........................... 602/43 |
| 2008/0063695 A1 * | 3/2008 | Vitaris ........................... 424/443 |
| 2014/0309575 A1 * | 10/2014 | Apolet et al. ................... 602/48 |

* cited by examiner

WOUND DRESSING

CROSS-REFERENCE TO RELATED APPLICATION

This application claims priority from and benefit of U.S. Provisional Application Ser. No. 61/635,320, file Apr. 19, 2012, entitled "RENEWAL RAIN DEVICE FOR WOUND DRESSING," which application is incorporated herein in its entirety by reference.

TECHNICAL FIELD

The invention relates to wound dressings. More particularly, the invention relates to a wound dressing including a highly absorbent layer capable of keeping a wound clean and dry.

BACKGROUND OF THE INVENTION

People may have surgical wounds resulting from various medical procedures. For example, large incisions are made into the skin for exploratory surgery or the removal of tissue. People may have skin ulcers from various causes. Accidental injuries are sometimes repaired with stitches extending over large sections of the skin. Wounds result from injuries on a battlefield. In addition, wounds can result from surgically implanted, indwelling catheters used in connection with a variety of procedures. Many diabetic patients use indwelling catheters for delivering insulin. Patients undergoing long term chemotherapy also may have an indwelling catheter. Peritoneal dialysis patients use an indwelling peritoneal catheter for delivering dialysis fluid. All of these wounds require proper care to avoid infection and to facilitate healing.

Protection of the wound is a significant daily task for these people. Infection of the wound must be avoided to prevent unintended complications. Traditional coverings for post-surgical wounds include bandages and gauze. One problem with these traditional coverings is the requirement that the coverings be frequently changed. Another problem is injury to the wound site caused by removal of the covering. Other problems include increased risk of infection and maceration of the skin due to continuous exposure to moisture. The wounds need to be covered to keep the wound clean, dry and infection free. Generally, when a person with a surgical wound dressing wants to swim, shower or bathe, the person tries to protect the wound site against moisture by using makeshift plastic covers taped over the exposed wound. These makeshift covers often fail to work, allowing moisture to enter the wound site. They are not designed to affirmatively repel or divert moisture away from the wound site. Usually, the person does not even know whether leakage has occurred until it is too late. These makeshift covers are simply inadequate to protect the wound site against moisture and the risk of serious infection. If the covering leaks and the dressing becomes wet the dressing must be replaced so as not to inhibit healing of a wound covered by the dressing and/or to inhibit infection. Moisture can support the growth of harmful or infectious bacteria in and around the site.

The need exists for a moisture-proof barrier for use by people who must use indwelling catheters or have other wounds to prevent infection due to exposure to external sources of moisture. The need also exists for a wound covering which will absorb fluids from the wound site, but will keep the wound site dry.

SUMMARY OF THE INVENTION

The present invention provides an improved barrier which seeks to overcome the above mentioned problems. In accordance with one aspect of the present invention a wound dressing is provided which includes a base layer with a perimeter area. The base layer is resistant to penetration by liquids The base layer includes an inner adhesive band and an outer adhesive band and has an open area in a central portion of the base layer. The adhesive bands may be made from, for example, polyethylene tape. The inner adhesive band and the outer adhesive band have a non-adhesive space between them and are connected to each other by connection legs spaced around the non-adhesive space. The inner adhesive band, outer adhesive band and connection legs are covered by a removable protective layer, the protective layer has a plurality of perforations spaced about the protective layer with a plurality of non-perforated sections between the perforations. When the protective layer is removed, the perforations cause separation at the perforations and only one non-perforated section is removed at a time.

An inner layer includes an outer edge defining an inner layer area. The inner layer area includes a plurality of drain holes inward of the outer edge and spaced near the perimeter of the inner layer. In one embodiment, the inner layer is generally rectangular in shape and includes four sides and the plurality of drain holes are spaced such that each is generally centered on one of the four sides. The inner layer being resistant to penetration by liquids. An absorbent layer is adjacent the inner layer. The absorbent layer is preferably made from hydrophilic non-swelling foam, that is capable of absorbing and retaining fluids", but other suitable materials are possible. The absorbent layer may include a moister sensor, such as a cobalt strip to indicate that the absorbent layer has absorbed liquid.

An outer layer is adjacent the absorbent layer and is resistant to penetration by liquids. The one of the inner layer and outer layer includes an adhesive band. The adhesive band defines an area inward of the adhesive band which is at least as large as the open area of the base layer. The adhesive band is covered by a removable protective layer. The protective layer has a plurality of perforations spaced about it with a plurality of non-perforated sections between the perforations such that when the protective layer is removed, the perforations cause separation at the perforations and only one non-perforated section is removed at a time. The outer layer is adapted to be placed over the open area of the base layer and to be attached to the base layer by the adhesive band of the outer layer.

In another embodiment, a wound dressing is provides which includes an inner layer with an outer edge defining an inner layer area. The inner layer area includes a plurality of drain holes inward of the outer edge and spaced near the perimeter of the inner layer. The inner layer is resistant to penetration by liquids. An absorbent layer is adjacent, but not attached to, the inner layer.

An outer layer is adjacent, but not attached to, the absorbent layer. The outer layer is resistant to penetration by liquids and includes an inner adhesive band, and an outer adhesive band. The inner adhesive band defines an area inward of the inner adhesive band which is at least as large as the inner layer area. The inner adhesive band and the outer adhesive band define a non-adhesive space between them and are connected by connection legs spaced around the non-adhesive space. The inner adhesive band, outer adhesive band and connection legs are covered by a removable protective layer which has a plurality of perforations spaced about the protective layer with a plurality of non-perforated sections between the perforations such that when the protective layer is removed, the perforations cause separation at the perforations and only one non-perforated section is removed at a time.

BRIEF DESCRIPTION OF THE SEVERAL VIEWS OF THE DRAWINGS

The foregoing and other objects, features, and advantages of the invention will be apparent from the following drawings and more particular description of the preferred embodiments of the invention.

DETAILED DESCRIPTION OF THE INVENTION

Throughout the following description, specific details are set forth in order to provide a more thorough understanding of the invention. However, the invention may be practiced without these particulars. In other instances, well known elements have not been shown or described in detail to avoid unnecessarily obscuring the disclosure. Accordingly, the specification and drawings are to be regarded as illustrative rather than restrictive. It is to be further noted that the drawings are not to scale.

Figure 1:
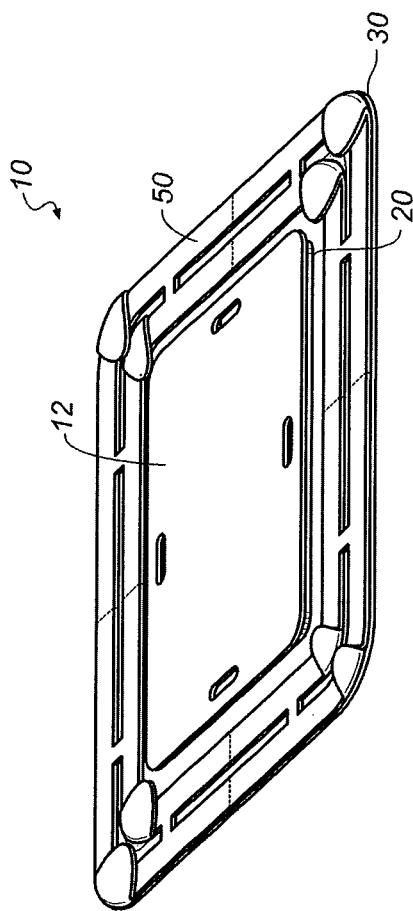
FIG. 1 is a perspective view of the present invention.
Figure 2:
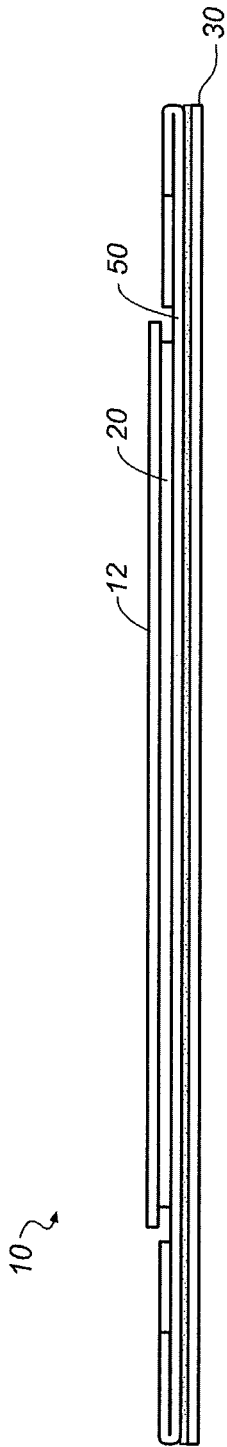
FIG. 2 is a front elevation view of the invention of FIG. 1.
Figure 3:
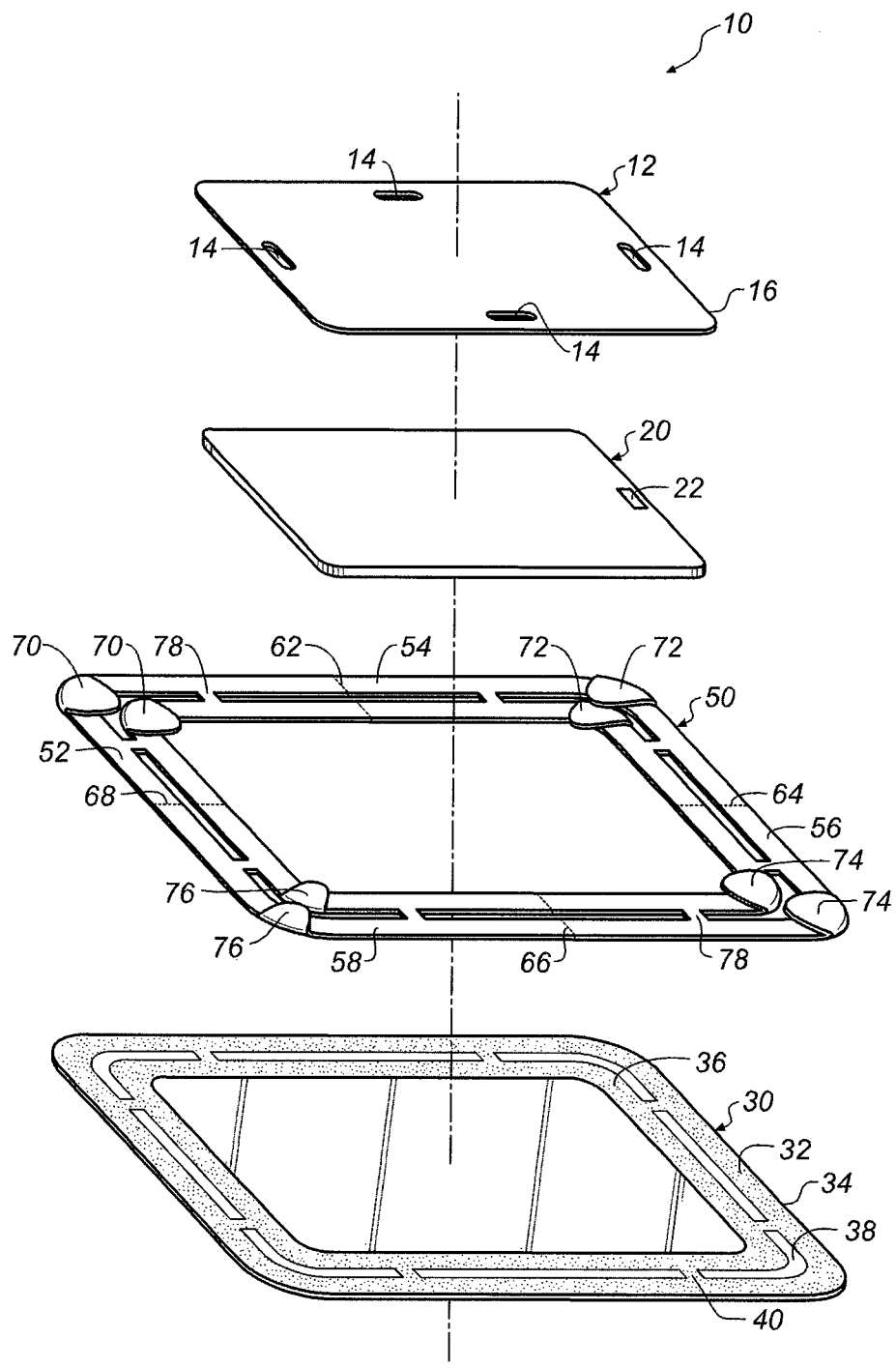
FIG. 3 is an exploded perspective view of the invention of FIG. 1.

FIGS. 1 through 3 illustrate a first embodiment of the invention. Referring to FIGS. 1 and 2, the wound dressing 10 includes an inner layer 12, an absorbent layer 20, an outer layer 30 and a backing layer 50.

Referring to FIG. 3, the inner layer 12 is constructed of a suitable material resistant to penetration by liquids, such as such as medical grade non-allergenic polyethylene, although other materials such as, for example, polyurethane, will work. Preferably, the inner layer 12 is between 1 and 2 mils thick, although thicknesses outside this range are acceptable. The inner layer 12 is shown as generally rectangular, but a variety of shapes are possible such as, square, round, oval or other suitable shapes. The inner layer 12 includes drainage holes 14 spaced about the perimeter 16 of the inner layer 12.

The absorbent layer 20 is preferably made from a material such as hydrocolloid, which is capable of absorbing liquids such as blood, exudate, and other liquids, entering through the drain holes 14. The absorbent layer 20 is sized such that it is no larger than the inner layer 12. The shape of the absorbent layer preferably generally conforms to that of the inner layer 12. Preferably, the absorbent layer 20 has a thickness of between 4 mm and 12 mm. The absorbent layer 20 can include a moisture indicator 22, such as, for example, a cobalt strip.

The outer layer 30 is constructed of a suitable material such as medical grade non-allergenic polyethylene which is resistant to penetration by liquids although other materials such as for example, polyurethane, will work. Preferably, the outer layer 30 is between 1 and 2 mils thick, although thicknesses outside this range are acceptable. The outer layer 30 is preferably larger than the inner layer 12. Preferably, the shape of the outer layer generally conforms to that of the inner layer 12. An outer adhesive band 32 is located near the perimeter 34 of the outer layer 30. An inner adhesive band 36 is placed inward from the outer adhesive band 32. The width of the outer adhesive band 32 and the inner adhesive band 36 will vary depending on the size of the wound dressing. Preferably, the adhesive band is made from medical grade, double-coated clear polyethylene tape with a non-sensitized acrylic pressure sensitive adhesive. Between the outer adhesive band 32 and the inner adhesive band 36 is a non-adhesive space 38. Legs 40 connect the outer adhesive band 32 and inner adhesive band 36 at various locations. The precise locations of the legs 40 may change depending on the size and shape of the wound dressing 10.

A removable protective backing 50 covers the outer adhesive band 32, the inner adhesive band 36 and the legs 40. Preferably, the protective backing 50 includes multiple sections 52, 54, 56 and 58 spaced about the protective backing 50 and perforated lines 62, 64, 66 and 68 between the sections 52, 54, 56 and 58. It will be understood by those of ordinary skill in the art that fewer or more sections will work equally as well. The removable protective backing 50 preferably includes tabs 70, 72, 74 and 76. The removable backing 50 also includes legs 78 corresponding to the legs 40 connecting the adhesive bands 32 and 36.

To place the wound dressing 10 over a wound, the protective backing 50 is pulled by one of the tabs 70, 72, 74 or 76. For example, section 52 is pulled away from outer adhesive band 32 and inner adhesive band 36. The section 52 breaks from the adjacent sections 54 and 58 at the perforations 62 and 68. The exposed portions of the outer adhesive band 32 and inner adhesive band 36 are placed on the skin (not shown). The process is repeated for the next sections 54 and 56. The last remaining section 58 is pulled off and the adhesive layer is attached to the skin (not shown), creating a seal and covering which is resistant to penetration by liquids from the outside. Because the adhesive bands 32 and 36 are placed on the skin (not shown) in sections, prior to the attachment of the last section, the relatively warmer air underneath the wound dressing 10 begins to move from the area underneath the wound dressing 10 to the area beyond the wound dressing 10, taking the warm moist air out from underneath the wound dressing 10.

Figure 4:
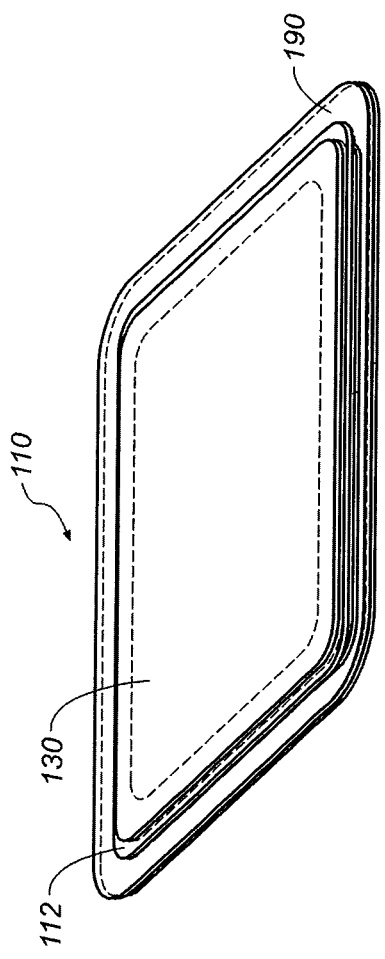
FIG. 4 is a perspective view of a second embodiment of the present invention.
Figure 5:
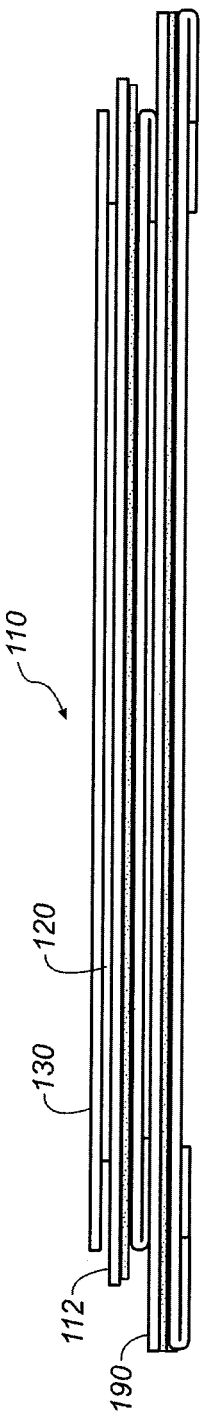
FIG. 5 is a front elevation view of the invention of FIG. 4.
Figure 6:
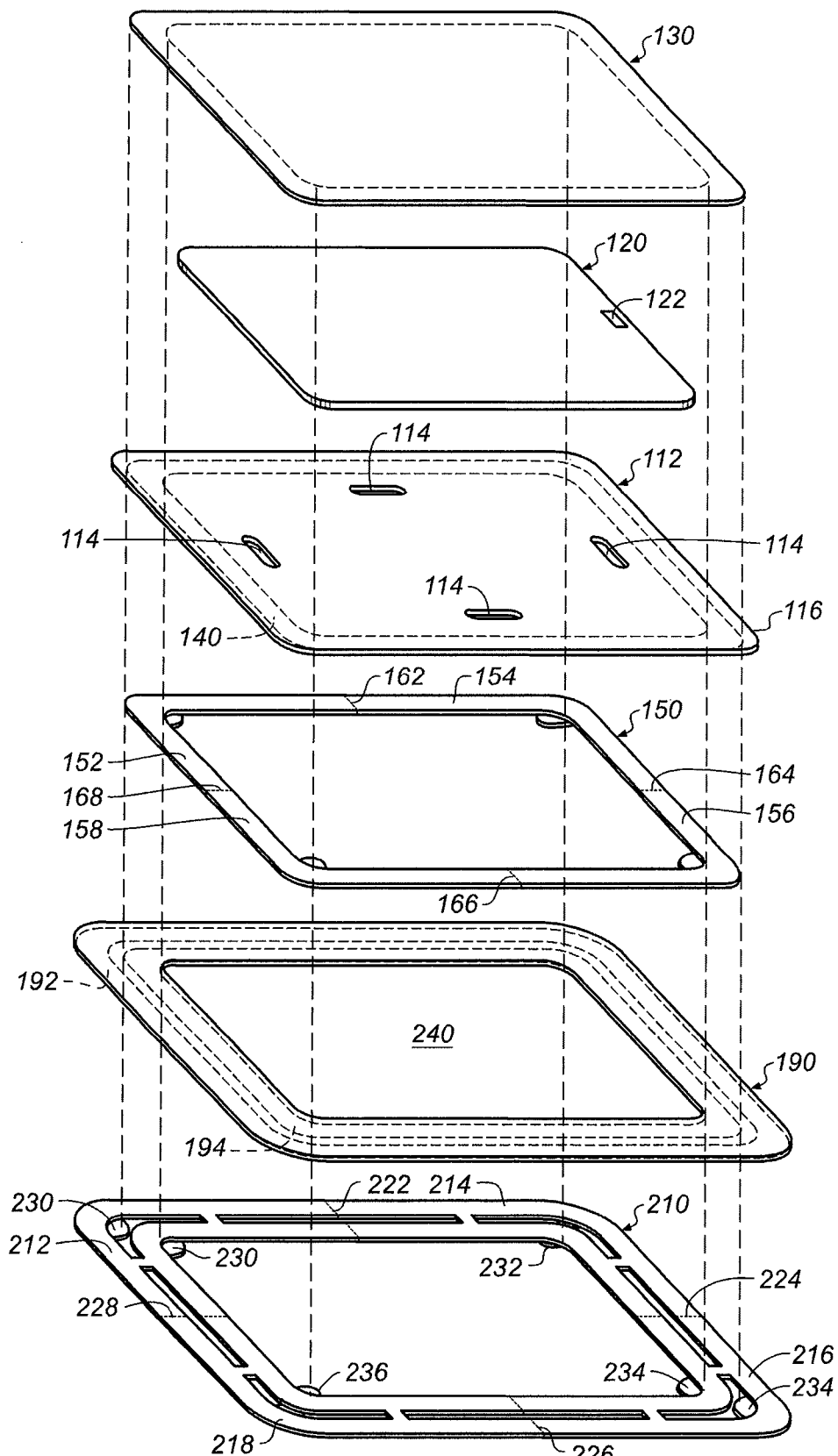
FIG. 6 is an exploded perspective view of the invention of FIG. 4.

FIGS. 4 to 6 illustrate a second embodiment of the invention. Referring to FIGS. 4 and 5, the wound dressing 110 includes an inner layer 112, an absorbent layer 120, an outer layer 130 and a base layer 190.

Referring to FIG. 6, the inner layer 112 is constructed of a suitable material resistant to penetration by liquids, such as medical grade non-allergenic polyethylene, although other materials such as, for example, polyurethane, will work. Preferably, the inner layer 112 is between 1 mil and 2 mils thick, although thicknesses outside of this range will work. The inner layer 112 is shown as generally rectangular, but a variety of shapes are possible such as, square, round etc. The inner layer 112 includes drainage holes 114 spaced about the perimeter 116 of the inner layer 112. Preferably, an adhesive band 140 is located near the perimeter 116 of the inner layer 112. It will be understood by those of ordinary skill in the art that the adhesive band 140 could be placed on the outer layer 130 instead of the inner layer 112. The width of the adhesive band 140 may vary depending on the size of the wound dressing.

The absorbent layer 120 is preferably made from a material capable of absorbing liquids such as a material such as hydrocolloid, which is capable of absorbing liquids such as blood, exudate, and other liquids. The absorbent layer 120 is sized such that it is no larger than the inner layer 112. Preferably, the absorbent layer 120 has a thickness of between 4 mm and 12 mm, although thicknesses outside this range will work. The absorbent layer 20 can include a moisture indicator 122, such as, for example, a cobalt strip The outer layer 130 is constructed of a suitable material such as medical grade non-allergenic polyethylene which is resistant to penetration by liquids although other materials such as, for example, polyurethane will work. Preferably, the outer layer 130 is between 1 mil and 2 mils thick, although thicknesses outside of this range will work.

A removable protective backing 150 covers the adhesive band 140. Preferably, the protective backing 150 includes multiple sections 152, 154, 156 and 158 spaced about the protective backing 150 and perforated lines 162, 164, 166 and 168 between the sections 152, 154, 156 and 158. It will be understood by those of ordinary skill in the art that fewer or more sections will work equally as well.

A base layer 190 is provided and includes an outer adhesive band 192 and an inner adhesive band 194. The base layer 190 has an open center area 240. A removable protective backing 210 covers the outer adhesive band 192, the inner adhesive band 194. Preferably, the protective backing 210 includes multiple sections 212, 214, 216 and 218 spaced about the protective backing 210 and perforated lines 222, 224, 226 and 228 between the sections 212, 214, 216 and 218. It will be understood by those of ordinary skill in the art that fewer or more sections will work equally as well. The removable protective backing 150 preferably includes tabs 230, 232, 234 and 236.

To place the wound dressing 110 over a wound, protective backing layer section 212 is removed by pulling on tab 230. Protective backing layer section 212 will break away from sections 214 and 218 at perforations 222 and 228. The exposed portion of adhesive bands 192 and 194 are placed on the skin (not shown). The remaining sections of the adhesive bands 192 and 194 are placed on the skin the same manner.

Next, the removable protective backing 150 is removed from the adhesive band 140 on the inner layer 112. The inner layer 112 is placed so that it covers the open center area 240 and the adhesive band 140 attaches to the base layer 190.

As will be apparent to those skilled in the art in light of the foregoing disclosure, many alterations and modifications are possible in the practice of this invention without departing from the spirit or scope thereof.

What is claimed is:

1. A wound dressing comprising:
   a base layer having a perimeter area, the base layer being resistant to penetration by liquid, the base layer including an inner adhesive band, and an outer adhesive band, the base layer defining an open area in a central portion of the base layer, the inner adhesive band and the outer adhesive band defining a non-adhesive space between the inner adhesive band and the outer adhesive band, the inner adhesive band and the outer adhesive band connected to one another through connection legs spaced around the non-adhesive space, the inner adhesive band, outer adhesive band and connection legs covered by a removable protective layer, the protective layer having a plurality of perforated lines spaced about the protective layer with a plurality of non-perforated sections between the perforated lines such that when the protective layer is removed, separation occurs at the perforated lines and only one non-perforated section is removed at a time;
   an inner layer, the inner layer having an outer edge defining an inner layer area, the inner layer area including a plurality of drain holes inward of the outer edge and spaced near the perimeter of the inner layer, the inner layer being resistant to penetration by liquid;
   an absorbent layer adjacent the inner layer; and
   an outer layer adjacent the absorbent layer and attached to the inner layer, the outer layer being resistant to penetration by liquid, at least one of the inner layer and the outer layer including an attachment adhesive band, the attachment adhesive band surrounding an area inward of the attachment adhesive band, the area being at least as large as the open area of the base layer, the attachment adhesive band covered by a removable protective layer, the protective layer having a plurality of perforated lines spaced about the protective layer with a plurality of non-perforated sections between the perforated lines such that when the protective layer is removed, separation occurs at the perforated lines and only one non-perforated section is removed at a time, the outer layer adapted to be placed over the open area of the base layer and to be attached to the base layer by the attachment adhesive band.

2. The wound dressing of claim 1 wherein the absorbent layer is made from hydrocolloid.

3. The wound dressing of claim 1 wherein the inner layer is generally rectangular in shape and includes four sides, the plurality of drain holes are spaced such that each is generally centered on one of the four sides.

4. The wound dressing of claim 1 wherein the inner layer is made from polyethylene.

5. The wound dressing of claim 1 wherein the outer layer is made from polyethylene.

6. The wound dressing of claim 1 wherein the attachment adhesive band is made from polyethylene adhesive tape.

7. The wound dressing of claim 1 wherein the base layer is made from polyethylene.

8. The wound dressing of claim 1 further including a moisture sensor between the outer layer and the absorbent layer.

9. The wound dressing of claim 8 wherein the moisture sensor comprises a cobalt strip.

10. A wound dressing comprising:
    an inner layer, the inner layer having an outer edge defining an inner layer area, the inner layer area including a plurality of drain holes inward of the outer edge and spaced near the perimeter of the inner layer, the inner layer being resistant to penetration by liquid;
    an absorbent layer adjacent, but not attached to, the inner layer; and
    an outer layer adjacent, but not attached to, the absorbent layer, the outer layer being resistant to penetration by liquid, the outer layer including an inner adhesive band and an outer adhesive band, the inner adhesive band surrounds an area at least as large as the inner layer area, the inner adhesive band and the outer adhesive band defining a plurality of non-adhesive spaces between the inner adhesive band and the outer adhesive band, the inner adhesive band and the outer adhesive band connected to one another through connection legs, each connection leg being located between adjacent non-adhesive spaces, the inner adhesive band, outer adhesive band and connection legs covered by a removable protective layer, the protective layer having a plurality of perforated lines spaced about the protective layer with a plurality of non-perforated sections between the perforated lines such that when the protective layer is removed, separation occurs' at the perforated lines and only one non-perforated section is removed at a time.

11. A wound dressing comprising:
    a base layer having a perimeter area, the base layer being resistant to penetration by liquid, the base layer including an inner adhesive band, and an outer adhesive band, the base layer defining an open area in a central portion of the base layer, the inner adhesive band and the outer adhesive band defining a non-adhesive space between the inner adhesive band and the outer adhesive band, the inner adhesive band and the outer adhesive band connected to one another through connection legs spaced around the non-adhesive space, the inner adhesive band, outer adhesive band and connection legs covered by a removable protective layer, the protective layer having a plurality of perforated lines spaced about the protective layer with a plurality of non-perforated sections between the perforated lines such that when the protective layer is removed, separation occurs at the perforated lines and only one non-perforated section is removed at a time;

an inner layer, the inner layer having an outer edge defining an inner layer area, the inner layer area including a plurality of drain holes inward of the outer edge and spaced near the perimeter of the inner layer, the inner layer being resistant to penetration by liquid;

an absorbent layer adjacent the inner layer; and an outer layer adjacent the absorbent layer and attached to the inner layer, the outer layer being resistant to penetration by liquid, the inner layer including an attachment adhesive band, the attachment adhesive band surrounding an area inward of the attachment adhesive band, the area being at least as large as the open area of the base layer, the attachment adhesive band covered by a removable protective layer, the protective layer having a plurality of perforated lines spaced about the protective layer with a plurality of non-perforated sections between the perforated lines such that when the protective layer is removed, separation occurs at the perforated lines and only one non-perforated section is removed at a time, the outer layer adapted to be placed over the open area of the base layer and to be attached to the base layer by the attachment adhesive band.

12. A wound dressing comprising:

a base layer having a perimeter area, the base layer being resistant to penetration by liquid, the base layer including an inner adhesive band, and an outer adhesive band, the base layer defining an open area in a central portion of the base layer, the inner adhesive band and the outer adhesive band defining a non-adhesive space between the inner adhesive band and the outer adhesive band, the inner adhesive band and the outer adhesive band connected to one another through connection legs spaced around the non-adhesive space, the inner adhesive band, outer adhesive band and connection legs covered by a removable protective layer, the protective layer having a plurality of perforated lines spaced about the protective layer with a plurality of non-perforated sections between the perforated lines such that when the protective layer is removed, separation occurs at the perforated lines and only one non-perforated section is removed at a time;

an inner layer, the inner layer having an outer edge defining an inner layer area, the inner layer area including a plurality of drain holes inward of the outer edge and spaced near the perimeter of the inner layer, the inner layer being resistant to penetration by liquid;

an absorbent layer adjacent the inner layer; and an outer layer adjacent the absorbent layer and attached to the inner layer, the outer layer being resistant to penetration by liquid, the outer layer including an attachment adhesive band, the attachment adhesive band surrounding an area inward of the attachment adhesive band, the area being at least as large as the open area of the base layer, the attachment adhesive band covered by a removable protective layer, the protective layer having a plurality of perforated lines spaced about the protective layer with a plurality of non-perforated sections between the perforated lines such that when the protective layer is removed, separation occurs at the perforated lines and only one non-perforated section is removed at a time, the outer layer adapted to be placed over the open area of the base layer and to be attached to the base layer by the attachment adhesive band.

\* \* \* \* \*